United States Patent [19]

Guillemin et al.

[11] 4,165,284

[45] Aug. 21, 1979

[54] SAFETY DEVICE FOR CHROMATOGRAPHY APPARATUS

[75] Inventors: Claude Guillemin, Paris; Christian Mayen, Creteil, both of France

[73] Assignee: Prolabo, Paris, France

[21] Appl. No.: 881,918

[22] Filed: Feb. 28, 1978

[30] Foreign Application Priority Data

May 2, 1977 [FR] France .................................. 77 13999

[51] Int. Cl.² ............................................. B01D 15/08
[52] U.S. Cl. ................................... 210/198 C; 55/386
[58] Field of Search ............ 210/31 C, 198 C; 55/67, 55/386

[56] References Cited

U.S. PATENT DOCUMENTS

| | | |
|---|---|---|
| 3,150,517 | 9/1974 | Kuffer et al. ....................... 55/386 X |
| 3,223,123 | 12/1965 | Young .................................. 55/67 X |
| 3,364,659 | 1/1968 | Pierrard et al. ..................... 55/386 X |
| 3,524,305 | 8/1970 | Ives ......................................... 55/386 |
| 3,650,090 | 3/1972 | Temale et al. ........................ 55/67 X |
| 3,807,217 | 4/1974 | Wilkins ................................. 55/67 X |

*Primary Examiner*—John Adee
*Attorney, Agent, or Firm*—Bacon & Thomas

[57] ABSTRACT

A safety device for distributing the carrier liquid of a chromatography apparatus having a carrier liquid source, a carrier liquid reservoir provided with an entrance and an outlet, an overflow conduit, a conduit for conveying the carrier liquid toward the chromatography apparatus, and three interdependently controlled valves respectively located between the exit of the reservoir and the overflow conduit, between the entrance of the reservoir and the carrier liquid source, and between the carrier gas source and the reservoir exit. The device is usable for distributing the carrier liquid of a liquid-phase chromatography apparatus wherein the carrier liquid is pushed by a carrier gas.

8 Claims, 4 Drawing Figures

SAFETY DEVICE FOR CHROMATOGRAPHY APPARATUS

BACKGROUND OF THE INVENTION

This invention is in the field of safety devices for distributing the carrier liquid of a liquid-state chromatography apparatus.

A liquid-state chromatography apparatus successively comprises, in the direction of flow:
 (1) a reservoir for carrier liquid;
 (2) a carrier liquid pumping system, which supplies the carrier liquid to the separation column;
 (3) a system column within which separation takes place, that is, where the sample is separated into its various components;
 (4) a detector, of a type depending upon the molecules to be detected.

The separation column should be traversed by the carrier liquid at a low but constant rate of flow. In view of the substrate and length of the column, the head loss must be compensated by application of pressure on the carrier liquid upstream of the separation column. The use of pumps is avoided in the carrier liquid feed system of the usual chromatography apparatuses, since they are often fragile and expensive, and such pumps are the source of vibrations which lead to uneven flow of the carrier liquid and to background noise at the detector baseline. Thus, the use of pumps may be avoided by keeping the reservoir containing the carrier liquid under the pressure of a carrier gas of low solubility in the carrier liquid, the gas being contained in a compressed gas cylinder and furnished through a pressure regulator. It is necessary in this case to prevent the gas from mixing with the carrier liquid, which involves the risk of creating an emulsion at the exit from the column. The carrier liquid reservoir most often consists of a tube of small diameter wound helically to reduce its bulk. This reservoir arrangement reduces the contact area between the carrier liquid and the carrier gas, and the substantial length of the tube prevents bubbles of carrier gas from being driven to the base of the reservoir, from which base the carrier liquid is directed toward the separation column.

The use of a carrier gas requires certain precautions; its implementation is sensitive, particularly when the carrier liquid reservoir is being refilled. In fact, improper handling of the carrier liquid inlet valve, the overflow valve and the carrier gas inlet valve may result in premature emptying of the reservoir and forceful ejection of the carrier liquid.

SUMMARY OF THE INVENTION

The principal object of the present invention is to provide a device for distributing carrier liquid without mishandlings, that is, a device which prevents operation of one gate unless the others are in the appropriate position.

There has now been discovered a safety device for distribution of the carrier liquid of a liquid-state chromatography apparatus, said carrier liquid being propelled by a carrier gas, which device comprises the following elements:
 (1) a source of carrier liquid;
 (2) a reservoir for a carrier liquid, provided with an entrance and an exit;
 (3) an overflow conduit;
 (4) a first valve located between the entrance of said reservoir and said source of carrier liquid;
 (5) a second valve located between the exit of said reservoir and the overflow duct;
 (6) a source of carrier gas;
 (7) a third valve located between the source of carrier gas and the exit of the reservoir;
 (8) said valves being interdependently controlled;
 (9) connecting conduits between these various elements;
 (10) a conduit for transporting the carrier liquid from said device to the chromatography apparatus.

BRIEF DESCRIPTION OF THE DRAWINGS

The invention will be more readily understood with reference to the annexed drawings, which illustrate, merely as an example, a device embodying the invention.

DESCRIPTION OF A PREFERRED EMBODIMENT

Figure 1:
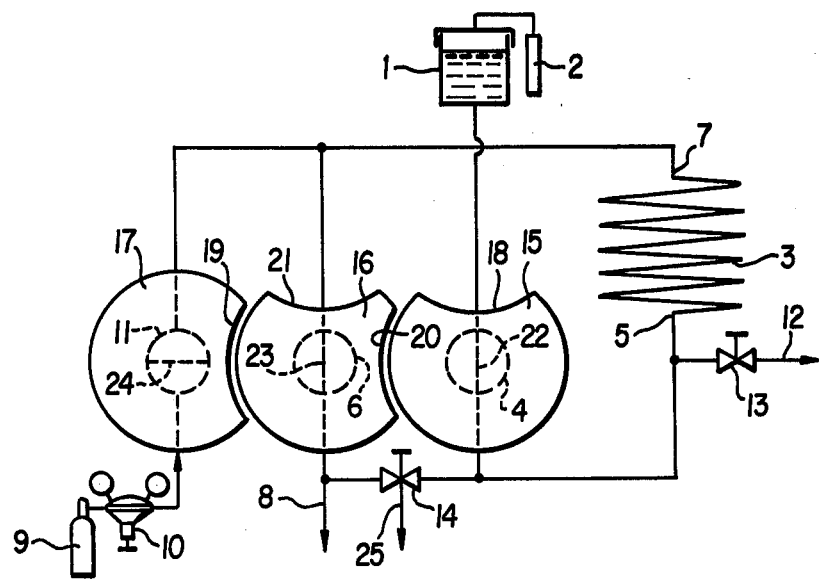
FIG. 1 schematically depicts the device as the carrier liquid reservoir is being filled.
Figure 3:
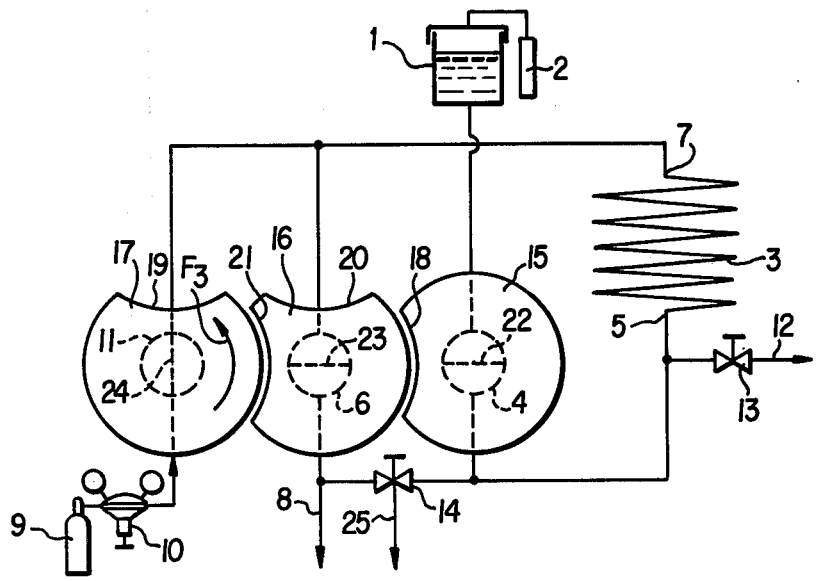
FIG. 3 schematically depicts the device as the carrier liquid is fed toward the chromatography apparatus.

The safety device according to the invention, for distributing the carrier liquid of a liquid-state chromatography apparatus wherein the carrier liquid is propelled by a carrier gas, is depicted in FIGS. 1, 2 and 3. It comprises, mainly:
 (1) a carrier liquid source 1 which may consist of a vessel which is open to the atmosphere through a drying device 2 of any conventional type;
 (2) a carrier liquid reservoir 3 consisting of a tube of small diameter wound helically to reduce both its bulk and the area of contact between the carrier liquid and the carrier gas;
 (3) a first valve 4 located in a conduit connecting the inlet 5 of the reservoir 3 and the carrier liquid source 1; said valve being operable to shut off the inlet 5 of the reservoir 3 from the carrier liquid source 1;
 (4) a second valve 6 located in a conduit connecting the outlet 7 of the reservoir 3 and the overflow duct 8 of the reservoir 3; said valve being operable to shut off the outlet 7 of the reservoir 3 from the overflow duct 8;
 (5) a compressed carrier gas source 9, provided with a pressure regulator 10;
 (6) a third valve 11 located in a conduit connecting the carrier gas source 9 and the outlet 7 of the reservoir 3; said valve being operable to shut off the exit 7 of the reservoir 3 from the carrier gas source 9.

It is understood that the several elements which comprise the device and are described above are linked by the connecting conduits referred to and that the device is provided with a further conduit 12 permitting the solvent to exit from the device toward the separation column of the chromatography apparatus. In addition, the carrier liquid distribution device is provided with two stopcocks; stopcock 13 is operable to shut off the device from the separation column of the chromatography apparatus, and stopcock 14 can be closed to shut off the inlet 5 of the reservoir 3 from the overflow pipe 8. Stopcock 14 is advantageously a three-way cock, to permit connecting the inlet 5 of the reservoir 3 to a drain conduit 25 in order to completely empty the reservoir 3.

According to the invention, the three valves 4, 6, 11 are controlled interdependently. Said interdependence is provided by interengaging means so arranged that no one of the valves can be operated unless the other two valves are in predetermined positions.

The interdependent control of the three valves can be accomplished, for example, by means of a programmer which acts on motors driving the valves. The programmer may be electronic or mechanical, such as cam actuated. Each valve may also be controlled by a clockwork system acting on the motors which actuate the valves.

A preferred mode of achievement of the device according to the invention makes use of mechanical means to effect the interdependence. One example of such a construction is depicted in FIGS. 1, 2 and 3. The mechanical means here consists of discs 15, 16 and 17 each of which is provided with at least one peripheral notch or cutout; said discs are respectively associated with the valves 4, 6 and 11 and are nested in such a fashion that the periphery of a disc extends into the cutout of an adjacent disc. Each cutout is of a shape complementary to the circular periphery of an adjacent disc so that the discs may be interengaged or "nested", as shown.

The valves 4, 6 and 11 may be quarter-turn valves, that is, valves which are opened by being rotated 90° from their closed position and which are advantageously provided with stops to limit their rotation, the discs 15, 16 and 17 being, respectively, directly attached to the shafts of the valves 4, 6 and 11. In FIGS. 1, 2 and 3, the valves are depicted by dashed lines. In the illustrated embodiment, the discs 15, 16 and 17 are of equal radius (R) and lie in the same plane; their centers are aligned and a distance d apart from each other such that R<d<2R. In order for discs lying in the same plane to be able to nest in the manner referred to, their peripheries must overlap each other; and in order for the discs to be able to be attached directly to the shafts of the valves, the centers of the discs must lie outside the peripheries of adjacent discs.

Disc 15 is provided with a cutout 18 complementary to the periphery of disc 16. Disc 16 is provided with two cutouts 20 and 21. Cutout 20 is complementary to the periphery of disc 15 and cutout 21 is complementary to the periphery of disc 17. Each cutout is symmetrical about an axis which is a diameter of the disc on which it is provided, and cutouts 20 and 21 of disc 16 are placed in such a fashion that their axes of symmetry are perpendicular to each other, cutout 21 being peripherally displaced 90° from cutout 20.

In order to facilitate determining of the position of the valves—that is, to verify whether they are open or closed—the valve channel conduits, which are generally cylindrical, have their axes in planes perpendicular to their respective discs, which planes each contain the axis of symmetry of a cutout. Thus, the axis of conduit 22 of valve 4 is contained in a plane which is perpendicular to disc 15 and contains the axis of symmetry of cutout 18. Similarly, the axis of conduit 23 of valve 6 lies in the plane which is perpendicular to disc 16 and contains the axis of symmetry of cutout 21, and the axis of conduit 24 of valve 11 lies in the plane perpendicular to disc 17 which contains the axis of symmetry of cutout 19.

The operation of the device according to the invention will now be described, with reference to FIGS. 1, 2 and 3, which together represent the various stages of operation of the three valves.

FIG. 1 depicts the first stage of operation of the three valves. Stopcocks 13 and 14 are closed and valves 4 and 6 are in the open position, that is, connection is established between the carrier liquid source 1 and the inlet 5 of the reservoir 3 and between the outlet 7 of the reservoir 3 and the overflow tube 8. Valve 11 is in the closed position, so that the carrier gas source 9 is shut off from the outlet 7 of the reservoir 3. The carrier liquid fills the reservoir 3; one may verify that said reservoir is full when the carrier liquid appears through the overflow tube 8. Discs 15 and 16 are interlocked by means of cutout 20 of disc 16 and discs 16 and 17 are interlocked by means of the cutout 19 of disc 17. Discs 16 and 17 are held stationary, preventing any operation of valves 6 and 11 unless valve 4 is first brought to the closed position.

Figure 2A:
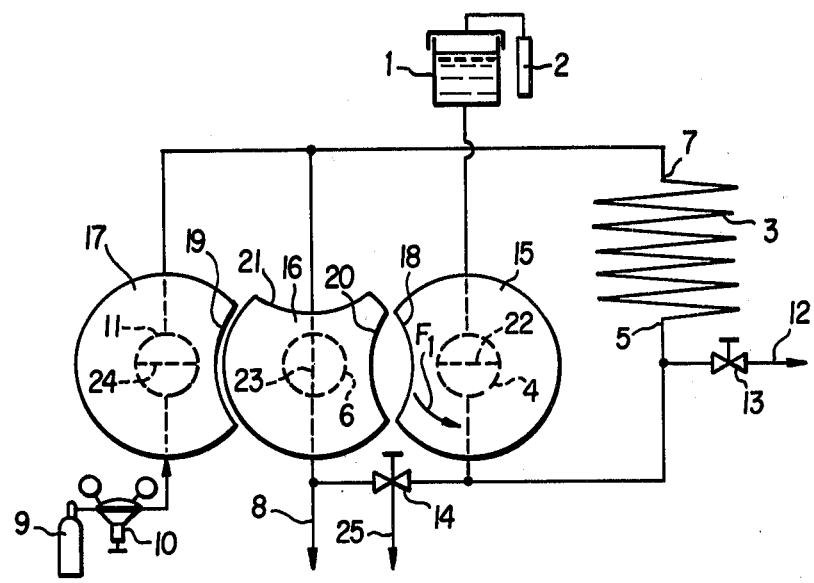
FIGS. 2a and 2b schematically depict two successive intermediate steps in the operation of the device according to the invention.

FIG. 2a depicts the second stage of operation of the valves. Stopcock 14 is closed and valve 4 is rotated a quarter turn in the direction indicated by arrow $F_1$; valve 4 is then in the closed position; the cutout 18 of disc 15 faces cutout 20 of disc 16, with the result that disc 16 may then turn. Valve 11 cannot be moved at this time.

Figure 2B:
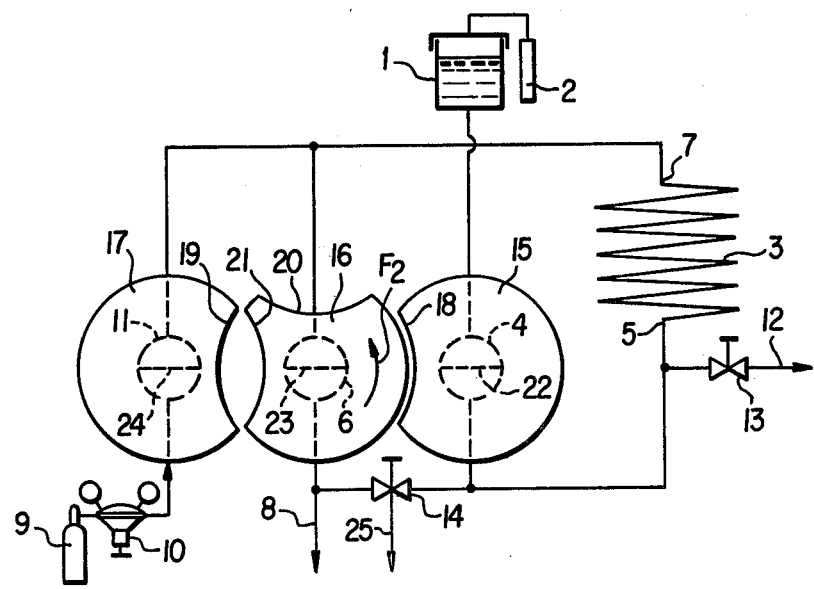

FIG. 2b shows the third stage of operation of valves. Valve 6 is rotated a quarter turn in the direction indicated by arrow $F_2$. Valve 6 is thus closed, and the exit 7 of the reservoir 3 is shut off from the overflow tube 8. Cutout 21 of disc 16 faces the cutout 19 of disc 17, with the result that disc 17 can now be rotated. Discs 15 and 16 are now interlocked by means of the cutout 18 of disc 15, and the valve 4 which is in the closed position can no longer be moved.

FIG. 3 depicts the fourth stage of the operation of the valves. Stopcock 13 is opened to provide a connection between the carrier liquid reservoir 3 and the chromatographic separation column. Valve 11 is rotated a quarter turn in the direction indicated by arrow $F_3$. Valve 11 is then open, establishing a connection between the carrier gas source 9 and the outlet 7 of the carrier liquid reservoir 3. The carrier gas forces the carrier liquid through conduit 12 toward the chromatographic separation column. Discs 16 and 17 are interlocked by means of cutout 21 of disc 16, and valve 6, which is closed, cannot be operated.

From the preceding description of the working of the safety device for distribution of the carrier liquid, it is evident, first, that the filling of the carrier liquid reservoir 3 takes place in complete safety, since when the carrier liquid inlet valve 4 is in its open position, the carrier gas inlet valve is in its closed position, shutting off the carrier gas source, and, second, the feeding of carrier liquid to the separation column also takes place in complete safety, since when the carrier gas inlet valve 11 is in its open position and the carrier liquid inlet valve 4 is in its closed position.

After the sample is analyzed, stopcock 13 is closed and valves 11, 6 and 4 are operated in the inverse procedure to the one described above.

Valves 4, 6 and 11 and discs 15, 16 and 17 then return to the position depicted in FIG. 1, and the carrier liquid reservoir 3 can again be filled.

It is advantageous to arrange at least two carrier liquid distribution devices in parallel so as to ensure a better utilization of the chromatographic separation column. For this purpose, stopcock 13 may be replaced, for example, by a three-way cock serving another assembly consisting of a carrier liquid reservoir and three valves associated to discs provided with cutouts, said assembly being similar to the one depicted in FIG. 1.

It is understood that, within the scope of the invention, the valves may be made interdependent by suitable means other than the discs described above such as by means of cams, gears, belts, or even a rod mechanism.

It is also understood that the three discs described above need not be aligned with each other and/or need not have the same radius. In order for two adjacent discs to be able to interlock by means of a cutout, the circles defining their peripheries must overlap each other. In general, then, two adjacent discs with radii R and R' respectively have their centers separated by a distance d such that $d < R + R'$. It is understood that such discs are provided with cutouts conforming to the radius of the discs adjacent to them.

The discs need not be mounted directly on the valve shafts, in which case a suitable system may be devised to link the valve shafts with the discs.

The device of this invention, for distributing the carrier liquid of a liquid-phase chromatography apparatus wherein the carrier liquid is propelled by a carrier gas, possesses the advantage of preventing improper operation of the valves. In fact, the interdependently controlled valves prevent all operation of any of them unless the other valves are in the appropriate positions.

The described device possesses the advantage of preventing the untimely emptying of the carrier liquid reservoir, accompanied by forceful ejection of the carrier liquid.

Moreover, the device according to the invention allows the operator to determine the position of the valves by simply looking at the front of the apparatus. In fact, discs marked with drawings of the valve conduits inside the valves may be mounted on the front panel as part of the display panel of the apparatus.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A safety device for a liquid-phase chromatography apparatus in which a carrier liquid is propelled by a carrier gas, said apparatus comprising a source of carrier liquid, a carrier liquid reservoir having an inlet and an outlet, an overflow conduit, a source of carrier gas, a first valve controlling a conduit connecting said source of carrier liquid to said inlet, a second valve controlling a conduit from said outlet to said overflow conduit, and a third valve controlling a conduit from said source of carrier gas to said outlet; the improvement comprising:
    said valves being separately operable valves;
    interlocking means between said first, second and third valves whereby operation of said valves is interdependent and wherein said interlocking means prevents operation of any selected valve when the other two valves are in other than predetermined positions.

2. A device as defined in claim 1 wherein said interlocking means prevents operation of any selected valve when the other two valves are in other than predetermined positions.

3. A device as defined in claim 1 wherein said interlocking means comprise mechanical connections between said valves.

4. A device as defined in claim 3 wherein said mechanical connections comprise: a rotatable disc fixed to each valve, each disc having a cutout in its periphery complementary to the periphery of an adjacent disc whereby when the periphery of one disc is nested in the cutout of an adjacent disc, that adjacent disc is held against rotation.

5. A device as defined in claim 4 wherein the distance between the centers of adjacent discs is less than the sum of the radii of said adjacent discs.

6. A device as defined in claim 4 wherein said discs are of the same radius and their centers are arranged on a straight line.

7. A device as defined in claim 4 wherein each cutout is symmetrical about a diameter of its disc, the discs on said first and third valves each having a single cutout and the disc on said second valve having two cutouts whose axes of symmetry are perpendicular to each other.

8. A device as defined in claim 7 wherein said valves are quarter-turn valves.

* * * * *